United States Patent
Massoud-Ansari et al.

(10) Patent No.: US 8,412,332 B2
(45) Date of Patent: Apr. 2, 2013

(54) MINIATURE WIRELESS SYSTEM FOR DEEP BRAIN STIMULATION

(75) Inventors: Sonbol Massoud-Ansari, El Dorado Hills, CA (US); Nader Najafi, Ann Arbor, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 1036 days.

(21) Appl. No.: 12/254,383

(22) Filed: Oct. 20, 2008

(65) Prior Publication Data

US 2009/0105784 A1    Apr. 23, 2009

Related U.S. Application Data

(60) Provisional application No. 60/999,397, filed on Oct. 18, 2007.

(51) Int. Cl.
*A61N 1/00* (2006.01)
*A61B 5/04* (2006.01)

(52) U.S. Cl. ............... 607/45; 607/30; 607/33; 607/36; 600/378

(58) Field of Classification Search ............ 607/30, 607/33, 36, 45; 600/378
See application file for complete search history.

(56) References Cited

U.S. PATENT DOCUMENTS

| | | | |
|---|---|---|---|
| 2004/0015199 A1* | 1/2004 | Thompson et al. | 607/36 |
| 2004/0267332 A1* | 12/2004 | Kast et al. | 607/61 |
| 2007/0060955 A1 | 3/2007 | Strother et al. | |
| 2007/0123938 A1* | 5/2007 | Haller et al. | 607/2 |
| 2007/0142872 A1* | 6/2007 | Mickle et al. | 607/45 |

OTHER PUBLICATIONS

Sorin Breit et al. 'Deep Brain Stimulation', Cell and Tissue Research, Aug. 2004, vol. 318, No. 1, pp. 275-288.

Maysam Ghovanloo et al. 'A Wireless Implantable Multichannel Microstimulating System-on-a-Chip With Modular Architecture', Neural Systems and Rehabilitation Engeering, IEEE Transaction, Sep. 2007, vol. 15, Issue 3, pp. 449-457.

* cited by examiner

*Primary Examiner* — Nicole F Lavert
(74) *Attorney, Agent, or Firm* — Hartman Global IP Law; Gary M. Hartman; Domenica N. S. Hartman

(57) ABSTRACT

An implantable system and method for deep brain stimulation (DBS) treatments. The implantable system is sufficiently small and self-contained to enable implantation of the entire system within the brain, or optionally within the brain and the surrounding tissue. The system comprises an implantable inductor on which a voltage is induced when subjected to an electromagnetic field, and an implantable device comprising a housing, stimulating elements at an exterior surface of the housing, and electronics within the housing and electrically connected to the implantable inductor. The electronics produces a brain-stimulating current from the voltage induced on the implantable inductor and then delivers the brain-stimulating current to the stimulating elements. Deep brain stimulation is performed by subjecting the inductor to an electromagnetic field to induce a voltage on the inductor that powers the electronics to produce and deliver the brain-stimulating current to the stimulating elements.

18 Claims, 2 Drawing Sheets

MINIATURE WIRELESS SYSTEM FOR DEEP BRAIN STIMULATION

CROSS REFERENCE TO RELATED APPLICATIONS

This application claims the benefit of U.S. Provisional Application No. 60/999,397, filed Oct. 18, 2007, the contents of which are incorporated herein by reference.

BACKGROUND OF THE INVENTION

The present invention generally relates to systems, devices and methods for a medical treatment known as deep brain stimulation (DBS). More particularly, the present invention relates to a miniature implantable DBS device capable of being entirely implanted within the brain and optionally the surrounding tissue.

DBS methods are used to stimulate the brain with electrical impulses to treat a variety of brain conditions and diseases, including but not limited to depression, Parkinson, stroke, essential tremor, dystonia, and tremor due to multiple sclerosis. DBS involves surgically implanting electrodes within the brain and then operating the electrodes to deliver electrical impulses capable of blocking certain activities in the brain, and particularly abnormal activity believed to cause undesirable conditions and symptoms. Programming of the deep brain stimulation treatment is easy and painless, and can offer patients relief from tremors, rigidity, slowness of movement, and stiffness, and may treat balance problems associated with their conditions. The level and duration of stimulation can be adjusted as a patient's condition changes over time.

DBS devices typically comprise a very thin insulated wire lead terminated with four electrode contacts. The lead is routed out of the skull through a small opening and connected to an extension wire subcutaneously routed along the head, neck, and shoulder to an impulse generator or other suitable neurostimulator device implanted under the skin, for example, in the chest area. As such, conventional DBS procedures and devices require two surgical procedures: a surgical procedure to implant the electrodes within the brain, and a second surgical procedure to implant the neurostimulator device in the chest.

The success of DBS is directly related to finding the specific area in the brain for stimulation. Consequently, during the brain surgery portion of the procedure the patient is only given a local anesthetic to numb the area to be operated on, and the patient remains awake and alert so that the surgeon can talk to the patient to ensure the proper areas of the brain are identified for stimulation. While the patient's head is immobilized with a special frame, two holes are drilled in the skull and, guided by imaging techniques, the surgeon implants electrodes to precisely targeted areas on each side of the brain. A neurologist and a neurosurgeon usually decide whether to target one of two areas commonly stimulated by DBS: either the subthalamic nucleus (STN) or the internal globus pallidus (GPi). These structures are deep within the brain and involved in motor control, and stimulation of these areas appears to block the signals that cause the disabling motor symptoms of the disease.

After the electrodes have been properly placed, the second surgical procedure is performed by which the surgeon implants the neurostimulator in the patient's chest, and the extension wire is routed beneath the patient's skin and connected to the electrode leads and the neurostimulator. Depending on the type of neurostimulator selected, two neurostimulators may be implanted to control symptoms affecting both sides of the body. Implantation of the neurostimulator is usually performed while the patient is under general anesthesia. Deep brain stimulation patients are often in the hospital for several days, and stimulation is usually initiated for the first time within a few weeks after implantation. The neurostimulator, which is usually battery powered, is programmed from outside the body to deliver a prescribed and usually continuous dosage of electrical impulses customized to the individual.

Because deep brain stimulation involves brain surgery, it can be appreciated that DBS procedures entail certain risks. The neurostimulator can also pose undesirable risks and side effects, due in part to the size of the neurostimulator. For example, an existing commercial unit used to control Parkinson's disease symptoms is about 7.5 cm wide and 1.3 cm thick, and contains a small battery and computer chip. Finally, there can be inconveniences associated with deep brain stimulation, including battery replacement and hardware malfunctions.

BRIEF DESCRIPTION OF THE INVENTION

The present invention provides an implantable system and method suitable for DBS treatments. The implantable DBS system is sufficiently small and self-contained to enable implantation of the entire DBS system within the brain, or optionally within the brain and the surrounding tissue. The DBS system can be implanted by a simple outpatient procedure, and therefore avoids the prior requirement for placing a patient under general anesthesia.

According to a first aspect of the invention, the system comprises an implantable inductor on which a voltage is induced when subjected to an electromagnetic field, and an implantable device comprising a housing, stimulating elements at an exterior surface of the housing, and electronics within the housing and electrically connected to the implantable inductor. The electronics produces a brain-stimulating current from the voltage induced on the implantable inductor and then delivers the brain-stimulating current to the stimulating elements. According to another aspect of the invention, deep brain stimulation is performed by implanting the inductor and device so that the device is within the brain, and then subjecting the inductor to an electromagnetic field to induce a voltage on the inductor that powers the electronics to produce and deliver the brain-stimulating current to the stimulating elements.

Significant advantages of this invention include the miniature size of the DBS device, simpler delivery and implantation (via an outpatient procedure and/or catheter delivery), and lower risks from the implantation procedure. Other advantages can include batteryless operation, reduced risks associated with side effects, additional functionality (for example, measurement of intracranial pressure (ICP), pH, neuro activities, or other physiological parameters), multiple stimulating probes at the same or different parts of the brain, and wireless communication.

Other objects and advantages of this invention will be better appreciated from the following detailed description.

DETAILED DESCRIPTION OF THE INVENTION

The present invention comprises a miniature implantable device and method for deep brain stimulation. The device contains all elements typically found in existing deep brain stimulation systems, including but not limited to neuro-leads (for example, pads, contacts, electrodes, etc.) and a neurostimulator. In contrast to existing deep brain stimulation systems, the device does not require a separate extension or neurostimulator that must be separately implanted. As such, the miniature integration achieved with the device avoids complications associated with prior art deep brain stimulation systems. The invention will be described in reference to embodiments of the invention depicted in FIGS. 1 through 8, in which consistent reference numbers are used to identify functionally similar structures.

Figure 1:
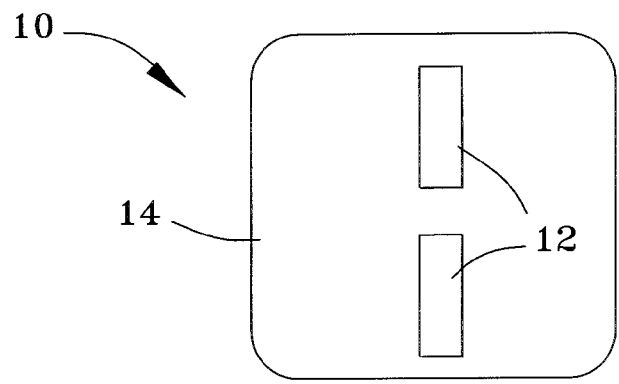
FIG. 1 represents a plan view of deep brain stimulation electrodes arranged on a surface of an implantable device in accordance with an embodiment of this invention.

FIG. 1 represents a plan view of an embodiment in which two brain-stimulating elements 12 (neural leads, pads, contacts, electrodes, etc.) are located on an outer surface 14 of a deep brain stimulation (DBS) device 10. The device 10, for example, any one of the embodiments shown in FIGS. 2 through 8, is capable of generating and delivering an electric current to the stimulating elements 12, for example, at levels consistent with prior art DBS systems. As shown in FIGS. 2 through 8, other electrode configurations can also be utilized and such variations in electrode configurations are intended to be encompassed by this invention. The stimulating elements 12 can be formed on the device surface 14 using a variety of processes, including deposition by electroplating, printing, or another process known in the art. The stimulating elements 12 can be formed to define a small gap therebetween, for example, about 0.1 to about 1000 micrometers. The stimulating elements 12 should be resistant to corrosion in the cerebral spinal fluid (CSF) within and surrounding the brain. For this reason, platinum, palladium, silver, titanium, and iridium alloys and silver oxide are believed to be well suited as materials for the stimulating elements 12. The stimulating elements 12 can also be passivated with a thin dielectric corrosion resistant layer.

Figure 2:
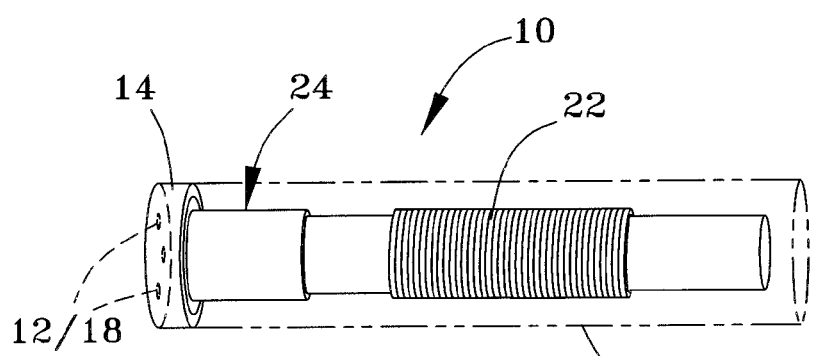
FIGS. 2 through 6 represent various embodiments for implantable deep brain stimulation devices in accordance with embodiments of this invention.
Figure 3:
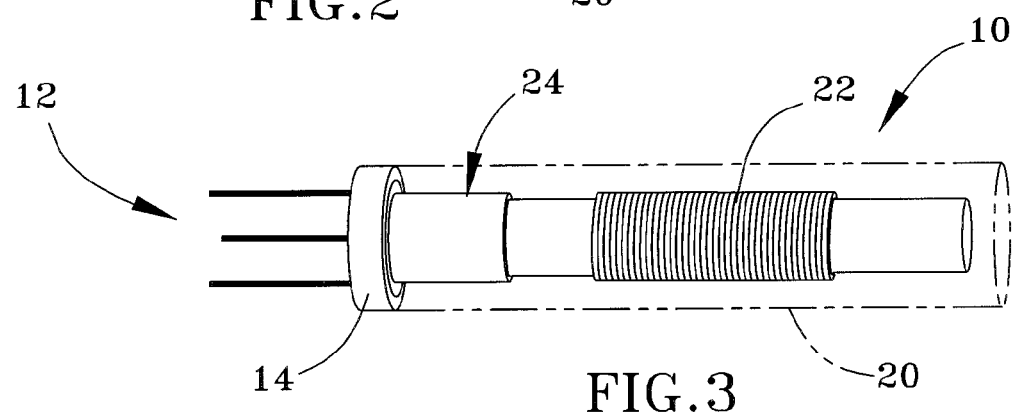

As evident from FIGS. 2 and 3, the stimulating elements 12 may have a variety of configurations, including two-dimensional structures (for example, flat pads or contacts) as shown in FIG. 2, and three-dimensional structures (for example, probes, etc.) that protrude from the device surface 14 as shown in FIG. 3. The stimulating elements 12 are connected to a coil assembly 22 (with an optional core) and electronics 24 (for example, printed circuit boards (PCBs), application-specific integrated circuits (ASICs), capacitor, diode, and/or other electrical components) within the device housing 20. The device 10 is preferably coupled via the coil assembly 22 to an external readout unit (not shown) capable of wirelessly providing radio frequency (RF) power to the device 10 and its electronics 24. The device 10 may further include a charge-storing device, such as capacitor or rechargeable battery capable of being charged and then discharged to provide the desired electric stimulating pulse. As such, the device 10 may contain a battery or may be batteryless.

The exterior of the device housing 20 can have a wide variety of configurations, including cylindrical exterior shapes as shown in FIGS. 2 and 3, as well as disk and planar exterior shapes. The housing 20 is preferably rigid and may be formed of a discrete component, such as a cylindrical glass tube or a coin-shape container with a hollow interior. Alternatively, the housing 20 may be defined by potting the components of the device 10 together using a suitable biocompatible potting material, such as an epoxy. Depending on its construction, the housing 20 can be made from a variety of other biocompatible materials, including ceramics, polymers, silicone, Parylene, etc.

In FIGS. 2 and 3, the DBS device 10 is represented as a sealed cylindrical-shaped capsule having a hollow interior in which the coil assembly 22 and electronics 24 are hermetically enclosed, with only the stimulating elements 12 exposed at the external surface 14 of the housing 20. The stimulating elements 12 are shown as located at the end of the cylindrical-shaped housing 20, though it is foreseeable that the stimulating elements 12 could be located elsewhere, for example, along the sides of the housing 20. The stimulating elements 12 and possibly some of the electronics 24 may be mounted on a substrate, connected together using various methods known in the art, for example, wirebonding, flexible connectors, etc., or potted together using a biocompatible epoxy or any other suitable potting material. The device surface 14 at which the stimulating elements 12 are disposed can be either rigid or flexible substrate material, or a combination (for example, a rigid-flex substrate, where part of the substrate is rigid and another part is flexible). In the case of flexible substrates, various polymers, Parylene, silicone, or other biocompatible flexible material may be used. In the case of rigid substrates, glass, silicon, ceramics, carbides, alloys, metals, hard polymers, Teflon, are some examples, although other types of materials can also be used. In the case of rigid-flex substrates, the rigid and flexible parts may be made from dissimilar material. The stimulating elements 12 themselves, especially three-dimensional stimulating elements 12, can also either be rigid, flexible, or a combination. For example the stimulating elements 12 can be formed by a flexible three-dimensional element made from polymers, Parylene, silicone, etc., which is partially or fully metallized. The stimulating elements 12 may also have a flexible tip portion connected to a rigid portion connected to the device surface 14, or alternatively may have a rigid tip portion connected to the surface 14 via a flexible portion. The rigid and flexible portions may be made from similar or dissimilar materials.

In some cases, it may be desirable to apply additional materials (organic, metal, or biocompatible material) to the exterior of the housing 20 to protect certain regions of the DBS device 10. For example, a coating may be applied to all but the stimulating elements 12, or the stimulating elements 12 may be coated with a material that differs from the material applied to the remainder of the housing 20. Examples of suitable coating materials include polymers, Parylene, silicone, hydrogels, titanium, nitrides, oxides, carbides, silicides, etc.

Figure 4:
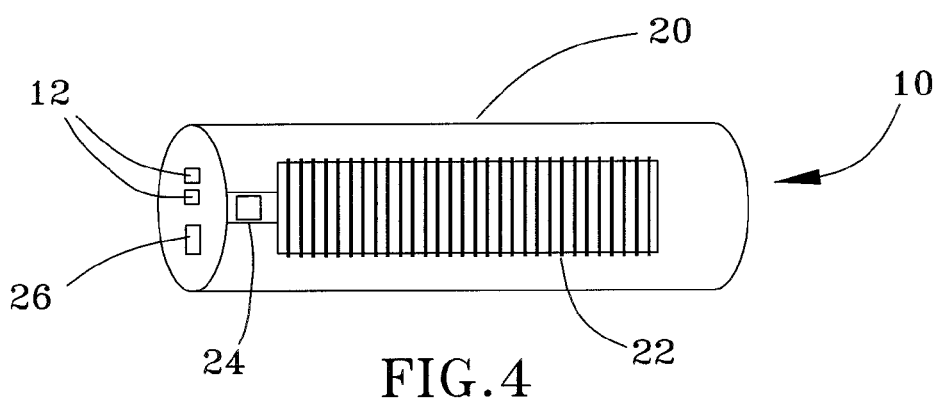
Figure 5:
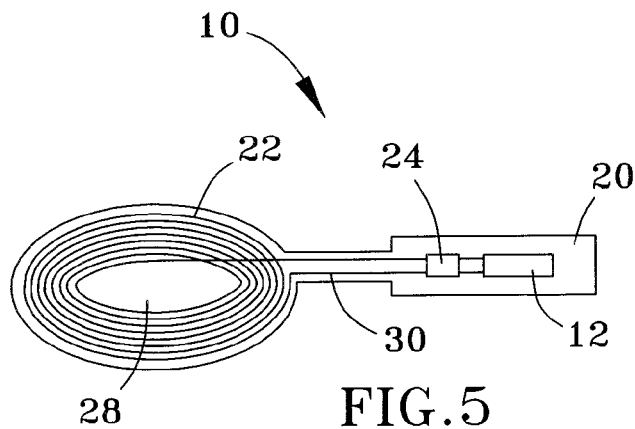
Figure 6:
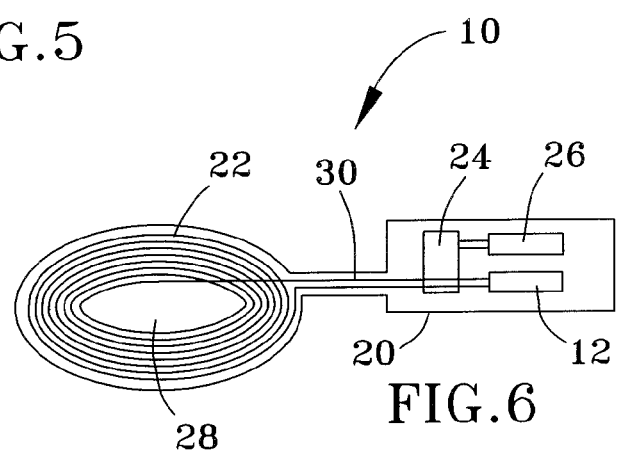
Figure 7:
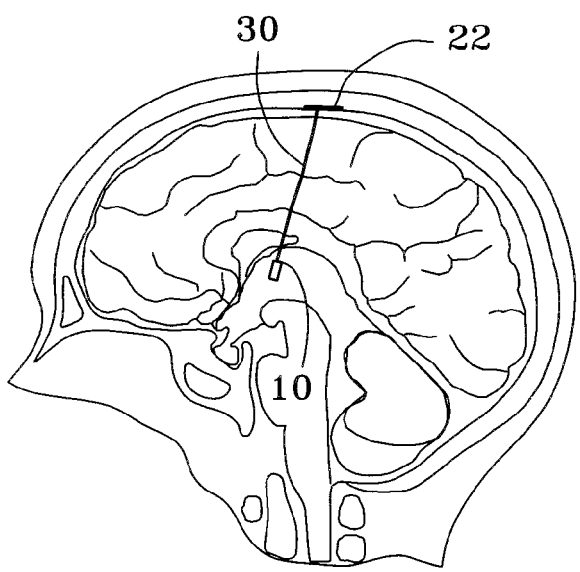
FIGS. 7 and 8 represent examples of intracranial placement of implantable deep brain stimulation devices of this invention.

The coil assembly 22 can be made using any method known in the art, such as winding a conductor around a ferrite core as represented in FIGS. 2 through 4 and 8, depositing (electroplating, sputtering, evaporating, screen printing, etc.) a conductive coil (preferably made from a highly conductive metal such as silver, copper, gold, etc.) on a rigid or flexible substrate 28 as represented in FIGS. 5 through 7), or any other method known to those skilled in the art. As such, the coil assembly 22 can be either flat or three-dimensional (cylindrical, cubic, etc.). An advantage of a flat coil configuration is that it can be easily implanted under the scalp such that the coil assembly 22 lies flat against the skull, as evident from FIG. 7.

The operation of the DBS device 10 can make use of a combination of powering and/or charging techniques and devices, including but not limited to wireless powering, one or more rechargeable or primary batteries, one or more capacitors, and/or one or more super capacitors. In a preferred embodiment, the device 10 employs a communication/telepowering scheme based on magnetic telemetry. Such schemes are disclosed in commonly-assigned U.S. Pat. Nos. 6,926,670 and 6,968,734 to Rich et al., whose contents are incorporated herein by reference. With such magnetic telemetry schemes, the device 10 preferably lacks an internal means for powering itself, and therefore lies passive in the absence of an external powering unit. When stimulation is desired, an external readout unit is brought within a suitable range of the device 10, and an inductor within the readout unit transmits an alternating electromagnetic (RF) field to the coil assembly 22 of the device 10 to induce a voltage capable of powering the device 10, as well as generate the brain-stimulating current for use by the stimulating elements 12. When sufficient voltage has been induced in the coil assembly 22, a supply regulator (rectification) circuitry within the electronics 24 of the device 10 converts the alternating voltage on the coil assembly 22 to a direct voltage that can be used by the electronics 24 as a power supply for signal conversion and communication, as well as deliver current to the stimulating elements 12 at an appropriate level for brain stimulation. At this point the DBS device 10 can be considered alert and may immediately deliver the brain-stimulating current to the elements 12 to initiate deep brain stimulation, or may await further commands from the readout unit prior to initiating deep brain stimulation. The readout unit may transmit either a continuous level of RF power to supply the device 10 with needed energy, or the readout unit may pulse the power allowing temporary storage in a battery or capacitor device within the device 10. The device 10 may work/stimulate continuously, or may do so periodically. In a periodic stimulation, one embodiment includes one phase for charging one or more charge-storing devices (such as capacitors, rechargeable batteries, etc.) and another phase for stimulating the brain. The charging and stimulating phases of the device operation may overlap.

As those skilled in magnetic telemetry are aware, a number of modulation schemes are available for transmitting data via magnetic coupling. Particularly suitable schemes include but are not limited to amplitude modulation, frequency modulation, frequency shift keying, phase shift keying, and also spread spectrum techniques. A preferred modulation scheme may be determined by the specifications of an individual application, and is not intended to be limited under this invention. In addition, many technologies exist that allow the device 10 to communicate signals to the readout unit via the coil assembly 22 or a second coil dedicated to signal transmission. Such signals can contain information obtained with the device 10, such as pressure, flow, pH, $CO_2$ levels, neuron activities, etc. The device 10 may transmit to the readout unit at any interval in time, delayed or instantaneous, during readout RF transmission or alternately in the absence of readout transmission.

In view of the above, the readout unit may further include signal reception, signal processing, and transmission circuitry for data analysis and subsequent communication. There are many techniques for construction of the readout coil and processing electronics known to those skilled in the art. The readout unit may interface to a display, computer, or other data logging device. In a preferred embodiment of the invention, the readout unit receives data from the DBS device 10 using the 13.56 MHz ISM band. Two modes of operation can be employed: (1) a data-logging measurement mode with optional data rates of, for example, 1 Hz and below, and (2) a real-time dynamic measurement mode with data rates of, for example, 100 to 500 Hz, for compliance and impulse tests. The readout unit may comprise analog RF front end electronics providing processing and user interface capabilities. A graphical user interface program can be used to control information (e.g., ICP monitor) and created in, for example, the LabVIEW and C visual programming languages.

The external readout unit can be adapted to perform one or more of the following: remote monitoring of patients, including but not limited to home monitoring; monitoring of patients with telephone-based (or similar method) data and information delivery; monitoring of patients with wireless telephone-based (or similar method) data and information delivery; monitoring of patients with web-based (or similar method) data and information delivery; closed-loop drug delivery to treat diseases; warning systems for critical worsening of diseases and related conditions; portable or ambulatory monitoring or diagnostic systems; battery-operation capability; data storage; reporting global positioning coordinates for emergency applications; communication with other medical devices including but not limited to pacemakers, defibrillator, implantable cardioverter defibrillator, implantable drug delivery systems, non-implantable drug delivery systems, and wireless medical management systems.

FIG. 4 is similar to FIGS. 2 and 3, but show the inclusion of a second element 26, which may be another sensing element adapted to sense a physiological parameter or an actuating element adapted to physically induce, stimulate, or respond to conditions within the brain or the cerebral spinal fluid. As nonlimiting examples, the DBS device 10 can further incorporate various other miniature sensing elements adapted to detect and/or monitor various physiological parameters of a patient, such as intracranial pressure (ICP), temperature, flow, velocity, vibration, acceleration, and/or measure specific chemistries such as gas content (e.g., $O_2$ and $CO_2$), and/or may incorporate various miniature actuators, including but not limited to thermal generators, voltage sources, current sources, probes, electrodes, drug delivery pumps, valves, meters, microtools for localized surgical procedures, and radiation emitting sources. Various specific examples of these types of miniature sensors and actuators are known to those skilled in the art, and any one or more of these can be utilized in the DBS device 10 of the present invention if capable of sufficiently small size to permit placement of the DBS device 10 within a catheter for delivery and implantation, or otherwise permit noninvasive surgical implantation. A particular example is to incorporate a pressure sensor into the device 10 for patients with traumatic brain injury to monitor brain pressure and allow for tailoring of the DBS treatment with the device 10. By measuring different physiologic parameters, the device 10 can use the measured physiologic parameter(s) to control, adjust or manipulate the stimulating function (for example, patter, frequency, location, amplitude, etc.). This approach allows dynamic and smart stimulation and allows the implementation of a closed-loop system. For example, if the second element 26 senses flow, the DBS device 10 can operate with other implanted or non-implanted devices (such as sensors, actuators, valves, etc.) as part of a closed-loop control system which can stimulate, monitor, measure one or more physiological parameter, and perform additional actions all based on feedback from one or more of other units in the closed-loop control system.

FIGS. 5 and 6 represent DBS devices 10 configured so that the housing 20 contains the stimulating elements 12, electronics 24, etc., and is adapted for deep implantation within the brain, whereas the coil assembly 22 is fabricated on a flexible or rigid film 28 that can be located remote from the device 10. The film 28 can be formed of any suitable biocompatible material, and is physically and electrically interconnected with the implantable housing 20 by a cable 30. The connection provided by the cable 30 may be flexible, rigid, or combination of flexible and rigid. The cable 30 may be coated, potted or covered with a biocompatible material. FIG. 6 differs from FIG. 5 by the inclusion of the second element 26, similar to FIG. 4.

Figure 8:
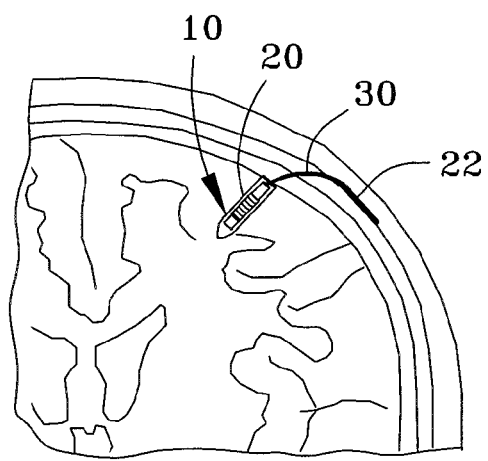

FIGS. 7 and 8 show DBS devices 10 of this invention comprising separate implantable housing and coil subassemblies, similar to FIGS. 5 and 6. In FIG. 8, the device 10 and its housing 20 are potted or coated, leaving only the stimulating elements 12 (not shown) in contact with the brain environment. The housing 20 is shown as having a conical distal tip to avoid snagging of vessels during insertion into the brain. In addition, the embodiment of FIG. 8 is provided with a cylindrical-shaped coil assembly 22 similar to the coil assemblies 22 of FIGS. 2 through 4. The coil assembly 22 (and any packaging thereof) can be attached to the skull and placed under the scalp, or attached under the skull above the dura mater such that it does not pierce the dura, or placed outside the body (for example, attached on top of the scalp). An advantage of the device configurations of FIGS. 5 through 8 is the ability for a very small footprint for the implanted portion of the DBS device 10 within the brain, while the bulkier coil assembly 22 is placed at a separate and possibly more favorable location. Other configurations are also foreseeable in which the brain stimulating elements 12 and possibly the electronics 24 of the DBS device 10 define an implantable subassembly, and the remaining components (including the coil assembly 22, some electronics, and possibly a battery or another charge-storing device) define a second subassembly that is attached at the scalp surface, and the two subassemblies are physically and electrically connected together with the cable 30.

Anchoring provisions may be incorporated directly into the housing 20, or added to the housing 20 by additional assembly steps. For example, the DBS device 10 could be inserted into a molded plastic or metal shell that incorporates anchoring provisions. Various other anchoring features and fasteners known in the art could also be used, including those adapted to attach to the skull or scalp using wires, screws (helical or otherwise), bolts, mesh, stents, springs, stitches, expandable tines, etc. Suitable anchoring mechanisms can also form part of another device with which the device 10 is implanted. For example, in patients with hydrocephalus, the anchoring mechanism can be part of the shunt used for draining the excess fluid. Suitable materials for anchors used with the device 10 include, but not limited to, Nitinol, Teflon, Parylene, polymers and metals.

According to a particularly desirable aspect of the invention, the device 10 is sufficiently small and self-contained to allow implantation using a surgical procedure or a minimally-invasive outpatient technique. A nonlimiting example of an exterior size for the housing 20 is about one-half centimeter in width/diameter and about one or two centimeters in length. The insertion and placement of the device 10 into the brain can be a relatively simple procedure and done by a trained technician rather than a highly specialized surgeon. This aspect of the invention is an important advantage over existing deep brain stimulation devices that require two surgical procedures: surgery on the brain to implant electrodes, and surgery on the chest under general anesthesia to implant a neurostimulator device.

In all applications, multiple DBS devices 10 may be used, either in close proximity or in separate locations. The multiple devices 10 may each be a completely separate unit and not share any common elements, or share a common coil assembly 22 or other device component. In some cases, the devices 10 may include or be used with multiple stimulating elements 12 on either the same or multiple different substrates.

The device 10 can be used in the treatment of many different diseases, including but not limited to cardiovascular disease, depression, Parkinson's disease, multiple sclerosis, amyotrophic lateral sclerosis (ALS, often referred to as "Lou Gehrig's disease") Alzheimer's, borderline personality, compulsive disorders, addictions, stroke, brain trauma, brain injury, inflammation in the brain, tumors, hydrocephalus, cerebral palsy, essential tremor, coma, mental retardation, dystonia, and tremor due to multiple sclerosis. The device 10 can significantly improve the tailored treatment of many severe diseases as a result of offering an easy to use and relatively low-cost option for performing non-invasive, real-time, detailed and chronic monitoring/stimulation at home, in the doctor's office, or in the hospital. In addition to the deep brain stimulation, implantable devices similar to the device 10 of this invention could also be used for different internal organs, including but not limited to the heart, kidneys, lungs, bladder, and abdomen.

While the invention has been described in terms of specific embodiments, it is apparent that other forms could be adopted by one skilled in the art. For example, the physical configuration of the device 10 could differ from that shown, and materials and processes other than those noted could be used. Therefore, the scope of the invention is to be limited only by the following claims.

The invention claimed is:

1. An implantable system for performing deep brain stimulation, the system comprising:
    an implantable inductor on which a voltage is induced when subjected to an electromagnetic field; and
    an implantable device comprising a housing, conductive stimulating elements located and formed on an exterior surface of the housing, and electronics within the housing and electrically connected to the implantable inductor, the electronics producing a brain-stimulating current from the voltage induced on the implantable inductor and then delivering the brain-stimulating current to the stimulating elements;
    wherein the housing and the stimulating elements are configured for deep brain implantation together;
    wherein the stimulating elements are spaced apart at the exterior surface of the housing and comprise at least two two-dimensional structures located and formed on the exterior surface of the housing or at least two three-dimensional structures that protrude through the exterior surface of the housing; and
    wherein the implantable inductor is entirely outside the housing of the device and has a flat coil configuration that enables the implantable inductor to be implanted separate from the housing and the stimulating elements, between the skull and the scalp and lie flat against the skull.

2. The system according to claim 1, wherein the implantable inductor is adapted for receiving the electromagnetic field from a non-implantable powering source.

3. The system according to claim 1, wherein the stimulating elements comprise the at least two two-dimensional structures located and formed on the exterior surface of the housing and do not protrude from the exterior surface of the housing.

4. The system according to claim 1, wherein the stimulating elements comprise the at least two three-dimensional structures that protrude through the exterior surface of the housing.

5. The system according to claim 1, wherein the housing has a hollow interior that contains the electronics of the implantable device.

6. The system according to claim 1, wherein the housing is a potted structure in which the electronics of the implantable device are potted.

7. The system according to claim 1, wherein the implantable inductor is connected to the housing by a cable.

8. The system according to claim 7, wherein the inductive coil is defined on a planar film.

9. The system according to claim 1, wherein the device further comprises an additional element adapted to sense a physiological parameter chosen from the group consisting of pressure, temperature, flow, velocity, vibration, acceleration, and chemistry, and the system uses the sensed physiologic parameter to control, adjust or manipulate the brain-stimulating current.

10. The system according to claim 1, wherein the device further comprises an actuator chosen from the group consisting of thermal generators, voltage sources, current sources, probes, electrodes, drug delivery pumps, valves, meters, microtools for localized surgical procedures, and radiation emitting sources.

11. A method of performing deep brain stimulation, the method comprising:
providing a device comprising a housing, electronics within the housing, conductive stimulating elements located and formed on an exterior surface of the housing, and an inductor entirely outside the housing and having a flat coil configuration, the stimulating elements being spaced apart at the exterior surface of the housing and comprising at least two two-dimensional structures located and formed on the exterior surface of the housing or at least two three-dimensional structures that protrude through the exterior surface of the housing, the electronics being electrically connected to the inductor and adapted to produce and deliver a brain-stimulating current to the stimulating elements;
implanting together the housing and the stimulating elements attached thereto deep within the brain;
implanting the inductor separately from the housing and the stimulating elements and between the skull and the scalp such that the inductor lies flat against the skull; and
subjecting the inductor to an electromagnetic field to induce a voltage on the inductor that powers the electronics to produce and deliver the brain-stimulating current to the stimulating elements.

12. The method according to claim 11, wherein the inductor receives the electromagnetic field from a non-implanted powering source.

13. The method according to claim 11, wherein the stimulating elements comprise the at least two two-dimensional structures located and formed on the exterior surface of the housing and do not protrude from the exterior surface of the housing.

14. The method according to claim 11, wherein the stimulating elements comprise the at least two three-dimensional structures that protrude through the exterior surface of the housing.

15. The method according to claim 11, wherein the inductor is connected to the housing by a cable.

16. The method according to claim 15, wherein the inductive coil is defined on a planar film.

17. The method according to claim 11, wherein the device further comprises an additional element that senses a physiological parameter chosen from the group consisting of pressure, temperature, flow, velocity, vibration, acceleration, and chemistry, and the method further comprises using the sensed physiologic parameter to control, adjust or manipulate the brain-stimulating current.

18. The method according to claim 11, wherein the device further comprises an actuator chosen from the group consisting of thermal generators, voltage sources, current sources, probes, electrodes, drug delivery pumps, valves, meters, microtools for localized surgical procedures, and radiation emitting sources.

* * * * *